United States Patent
Wilson et al.

(10) Patent No.: US 7,844,030 B2
(45) Date of Patent: Nov. 30, 2010

(54) SYSTEM AND METHOD OF FAST SWITCHING FOR SPECTRAL IMAGING

(75) Inventors: Colin R. Wilson, Niskayuna, NY (US); Antonio Caiafa, Niskayuna, NY (US); John Charles Hill, Georgetown, MA (US); Samit Kumar Basu, Fremont, CA (US); Pierfrancesco Landolfi, Palo Alto, CA (US); Peter Michael Edic, Albany, NY (US)

(73) Assignee: General Electric Company, Niskayuna, NY (US)

( * ) Notice: Subject to any disclaimer, the term of this patent is extended or adjusted under 35 U.S.C. 154(b) by 49 days.

(21) Appl. No.: 12/264,428

(22) Filed: Nov. 4, 2008

(65) Prior Publication Data

US 2009/0245467 A1 Oct. 1, 2009

Related U.S. Application Data

(60) Provisional application No. 61/039,466, filed on Mar. 26, 2008.

(51) Int. Cl.
*H05G 1/32* (2006.01)
*H05G 1/10* (2006.01)
*H05G 1/56* (2006.01)

(52) U.S. Cl. .................. 378/111; 378/101; 378/114

(58) Field of Classification Search ................ 378/91, 378/98, 98.9, 101, 111, 112, 114–116; 315/1, 315/107, 291; 314/115, 135; 363/59, 60; 307/112

See application file for complete search history.

(56) References Cited

U.S. PATENT DOCUMENTS

| 4,247,774 | A | 1/1981 | Brooks |
| 4,361,901 | A | 11/1982 | Daniels et al. |
| 5,490,196 | A | 2/1996 | Rudich et al. |
| 5,661,774 | A * | 8/1997 | Gordon et al. ........... 378/101 |
| 5,786,687 | A | 7/1998 | Faulk |
| 7,116,749 | B2 * | 10/2006 | Besson ................ 378/16 |
| 7,136,451 | B2 * | 11/2006 | Naidu et al. ............. 378/16 |
| 7,236,559 | B2 | 6/2007 | Jha et al. |
| 7,298,812 | B2 | 11/2007 | Tkaczyk et al. |
| 2004/0028181 | A1 * | 2/2004 | Charles, Jr. et al. ....... 378/92 |
| 2009/0180585 | A1 * | 7/2009 | Fujimoto et al. ........... 378/5 |

FOREIGN PATENT DOCUMENTS

| DE | 3447490 | 12/1984 |
| JP | 61054199 | 3/1986 |
| WO | 9202892 A1 | 2/1992 |
| WO | 2007017773 A2 | 2/2007 |

OTHER PUBLICATIONS

PCT Search Report—and written opinion—Jun. 29, 2009.

* cited by examiner

*Primary Examiner*—Edward J Glick
*Assistant Examiner*—Anastasia Midkiff
(74) *Attorney, Agent, or Firm*—Joseph J. Christian (57) ABSTRACT

A system includes a generator configured to output at least one voltage level and an x-ray source configured to generate x-rays directed toward an object. The system includes a module coupled to the output of the generator and to an input of the x-ray source and configured to switch or assist in switching an output to the x-ray source between a first voltage level and a second voltage level.

28 Claims, 5 Drawing Sheets

SYSTEM AND METHOD OF FAST SWITCHING FOR SPECTRAL IMAGING

CROSS-REFERENCE TO RELATED APPLICATION

The present application is a non-provisional of, and claims priority to, U.S. Provisional Application Ser. No. 61/039,466, filed Mar. 26, 2008, the disclosure of which is incorporated herein.

BACKGROUND OF THE INVENTION

The invention relates generally to diagnostic imaging and, more particularly, to a method and apparatus for fast dual-kVp switching in existing CT imaging systems.

Typically, in computed tomography (CT) imaging systems, an x-ray source emits a cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are quantized and transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam from a focal point. X-ray detectors typically include a collimator for collimating x-ray beams received at the detector, a scintillator adjacent the collimator for converting x-rays to light energy, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are quantized then transmitted to the data processing system for image reconstruction.

A CT imaging system may include an energy discriminating (ED), multi energy (ME), and/or dual energy (DE) CT imaging system that may be referred to as an EDCT, MECT, and/or DE-CT imaging system. The EDCT, MECT, and/or DE-CT imaging system is configured to be responsive to different x-ray spectra. For example, a conventional third-generation CT system may acquire x-ray projection data sequentially at different peak kilovoltage (kVp) levels of the x-ray source, which changes the peak and spectrum of energy of the incident photons comprising the emitted x-ray beams. Energy sensitive detectors may be used such that each x-ray photon reaching the detector is recorded with its photon energy.

Techniques to obtain the measurements include scanning with two distinctive energy spectra, and detecting photon energy according to energy deposition in the detector. EDCT/MECT/DE-CT provides energy discrimination and material characterization. For example, in the absence of object scatter, the system derives the behavior at a different energy based on the signal from two regions of photon energy in the spectrum: the low-energy and the high-energy portions of the incident x-ray spectrum. The detected signals from two energy regions provide sufficient information to resolve the energy dependence of the material being imaged. Furthermore, detected signals from the two energy regions provide sufficient information to determine the relative composition of an object composed of two hypothetical materials.

A principle objective of dual-energy scanning is to obtain diagnostic CT images that enhance contrast separation within the image by utilizing two scans at different energy spectra. For industrial inspection systems, the information allows characterization of the material-specific properties of scanned objects. A number of techniques have been proposed to achieve dual energy scanning, using a non-energy-discriminating detector such as a scintillator. Such techniques may include acquiring two scans either back-to-back sequentially in time where the scans require two rotations around the subject, or interleaved as a function of the rotation angle requiring one rotation around the subject, in which the tube operates at, for instance, 80 kVp and 140 kVp potentials. High frequency generators have made it possible to switch the potential of the x-ray source on alternating views. As a result, dual-energy projection data (high- and low-energy projection data) may be obtained in a temporally interleaved fashion, rather than two separate scans made several seconds apart, as required with previous CT technology. Taking separate scans at several seconds apart from one another results in mis-registration between datasets caused by patient motion (both external patient motion and internal organ motion) and, in the case of helical scanning such as used for inline object inspection, different cone angles. And, in general, a conventional two-pass dual kVp technique cannot be applied reliably where small details need to be resolved for body features or object features that are in motion, such as in a baggage scanner.

While switching the x-ray source potential via the high frequency generators solves many of the problems related to conventional two-pass dual-energy scanning, such a configuration does not always provide the switching speed needed for certain imaging applications. For example, cardiac imaging and certain low-current imaging applications such as security and industrial inspection cannot be effectively performed by simply switching the x-ray source potential with the high frequency generator. Often, there is a delay in the response time of the switched operating potential between the high frequency generator and the x-ray source, due in part to the capacitance of the cable and the x-ray tube connecting these devices, and the low x-ray tube current levels.

Using the dual-kVp switching technique described above, a high-voltage generator is coupled directly to an x-ray source, such as an x-ray tube, via a high-voltage cable. While the high-voltage generator may be a dual-stage generator capable of switching between two distinct voltage levels to perform dual-kVp imaging, this switching is typically affected by capacitive and other effects. That is, the rise time in switching the generator from a first (low) voltage, or first kVp, level to a second (high) kVp level is limited by the power of the high-voltage generator and may be too slow for effective dual-kVp imaging in many medical and security applications. Likewise, the fall time between switching the high kVp to a low kVp level is generally very slow, which effectively reduces the energy separation of the applied spectra, resulting in reduced material specification sensitivity and, therefore, the effectiveness of the dual-kVp imaging. As such, these insufficient switching speeds often lead to projection data pair mis-registration and streak artifacts in reconstructed images.

Therefore, it would be desirable to design an apparatus and method to provide suitable dual-kVp switching.

SUMMARY

The invention is a directed method and apparatus for fast kVp switching that overcome the aformentioned drawbacks.

According to one aspect of the invention, a system includes a generator configured to output at least one voltage level and an x-ray source configured to generate x-rays directed toward an object. The system includes a module coupled to the output of the generator and to an input of the x-ray source and configured to switch or assist in switching an output to the x-ray source between a first voltage level and a second voltage level.

According to another aspect of the invention, a method of acquiring imaging data at more than one energy spectrum includes inputting at least one voltage to a module, the module connectable to the x-ray source, and coupling the module to the x-ray source and outputting a first voltage to the x-ray source. The method further includes projecting a first beam of an x-ray energy spectrum toward the object from the x-ray source, generated using the first voltage, and acquiring a first set of measured projection data, switching from the first voltage to a second voltage using the circuit module, projecting a second beam of x-ray energy toward the object from the x-ray source, generated using the second voltage, and acquiring a second set of measured projection data, and reconstructing at least one representative image from the first and second sets of measured projection data.

According to yet another aspect of the invention an imaging system includes a gantry having an opening for receiving a subject to be scanned, an x-ray source configured to project x-rays having multiple energies toward the subject, a generator coupled to the x-ray source and configured to produce at least one voltage, a circuit module coupled between the generator and the x-ray source and configured to provide switching or assistance in switching between a first voltage and a second voltage such that x-rays having a first energy spectrum are generated when applying the first voltage and x-rays having a second energy spectrum are generated when the to applying the second voltage, and a computer. The computer is configured to acquire imaging data from x-rays at the first energy spectrum and at the second energy spectrum.

These and other advantages and features will be more readily understood from the following detailed description of preferred embodiments of the invention that is provided in connection with the accompanying drawings.

BRIEF DESCRIPTION OF THE DRAWINGS

FIG. 4 is a graphical representation of a fast kVp switching configuration according to an embodiment of the invention.

DETAILED DESCRIPTION OF PREFERRED EMBODIMENTS

The operating environment of embodiments of the invention is described with respect to a sixty-four-slice computed tomography (CT) system. However, it will be appreciated by those skilled in the art that embodiments of the invention are equally applicable for use with other multi-slice configurations. Moreover, embodiments of the invention will be described with respect to the detection and conversion of x-rays. However, one skilled in the art will further appreciate that embodiments of the invention are equally applicable for the detection and conversion of other high frequency electromagnetic energy. Embodiments of the invention will be described with respect to a "third generation" CT scanner, but are equally applicable with other generations of CT systems. Additional, the x-ray tube and detector are described to rotate around the object being imaged, but alternate configurations where the detector and x-ray source are held stationary and the object is rotated are also envisioned. Moreover, although discussed in the context of CT systems, these techniques are equally applicable to projection x-ray imaging used in medical and industrial radiographic applications as well.

Figure 1:
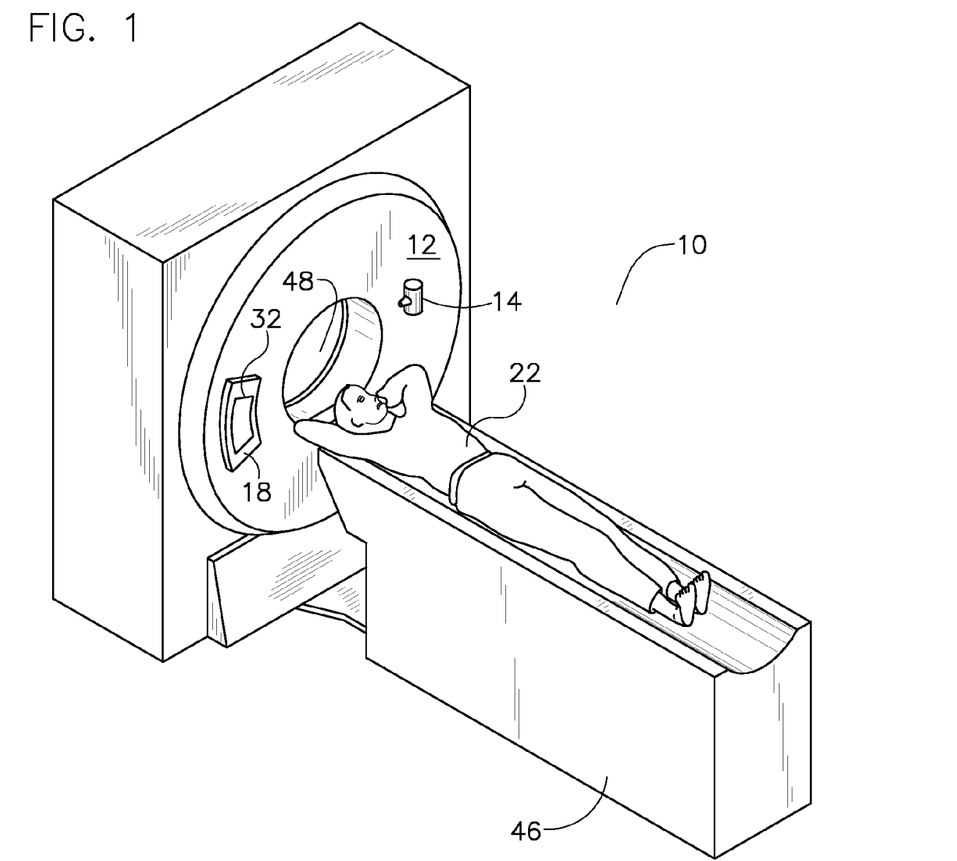
FIG. 1 is a pictorial view of a CT imaging system.
Figure 2:
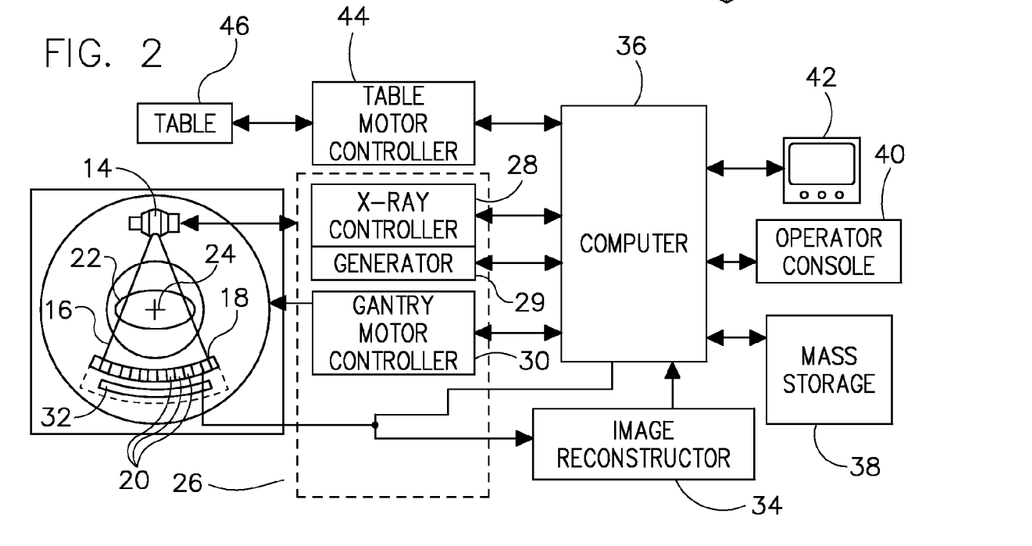

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to an x-ray source 14 and a gantry motor controller 30 that controls the rotational speed and position of gantry 12. An image reconstructor 34 receives sampled and digitized x-ray data from DAS 32 and performs high-speed reconstruction. The reconstructed image is applied as an input to a computer 36, which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
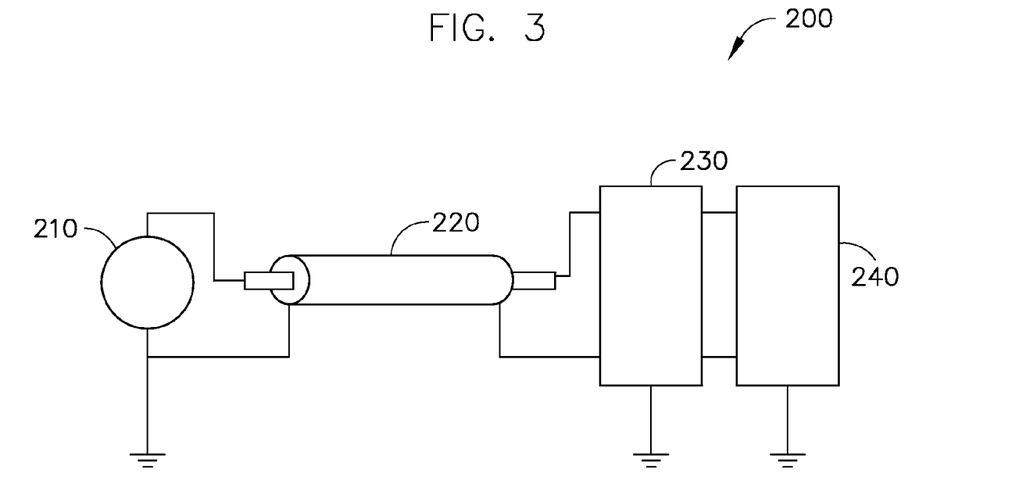
FIG. 3 is a schematic block diagram of a fast kVp switching configuration according to an embodiment of the invention.

Referring now to FIG. 3, an exemplary embodiment of a fast kVp switching configuration according to the invention is shown. System 200 includes a high-voltage generator 210 coupled to a high-voltage cable 220. High-voltage generator 210 is configured to produce at least one voltage level. System 200 includes an interposer circuit 230 coupled between high-voltage cable 220 and an x-ray tube 240. In embodiments of the invention, x-ray tube 240 may be a single-cathode or a dual-cathode x-ray tube, as examples. Interposer circuit 230 is configured to rapidly switch or assist in switching between a first voltage level and a second voltage level. This fast switching between the first voltage level and the second voltage level greatly decreases projection pairs mis-registration and resulting artifacts that may occur in reconstructed images, thereby improving material decomposition and effective atomic number determination of a scanned object.

Referring still to FIG. 3, as described above, interposer circuit 230 is coupled between high-voltage cable 220 and x-ray tube 240. With such a configuration, the load capacitance of the high-voltage cable 220 minimally affects the switching speed achievable by interposer circuit 230. The placement of interposer circuit 230, however, is not limited to the configurations shown in system 200. In embodiments of the invention, interposer circuit 230 can be constructed as a modular unit that may be incorporated into existing x-ray systems, including a generator of the x-ray system, under various configurations. Examples of such configurations will be discussed further herein. As a modular unit, the interposer circuit 230 may be put or built into an existing system, thus eliminating the need, in this example, for a complete overhaul or replacement of an x-ray system to enable fast dual-kVp imaging. Accordingly, by simply incorporating the modular interposer circuit 230 into an existing x-ray system, the costs typically associated with modifying or replacing the existing x-ray system for fast dual kVp imaging are greatly reduced.

Figure 4:
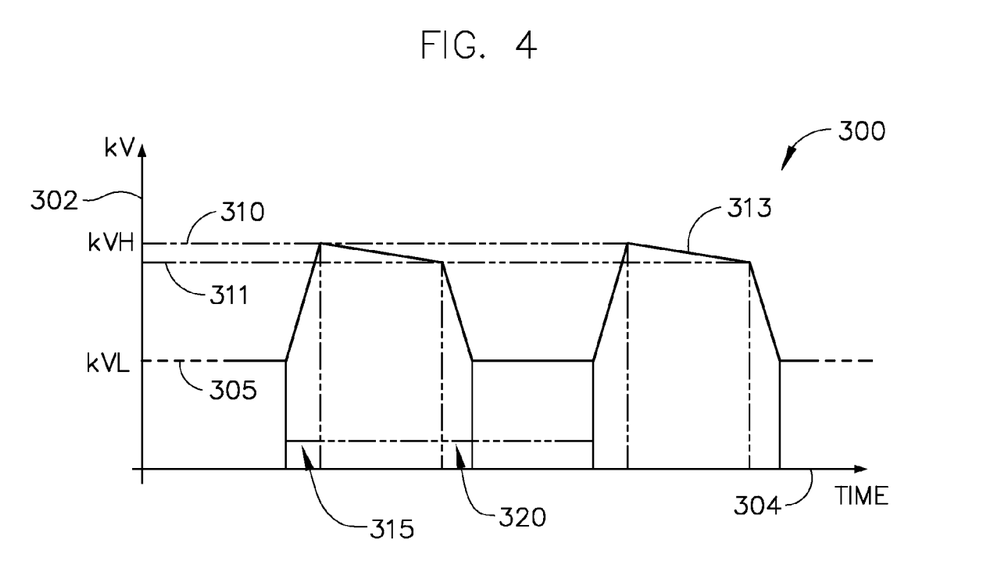
FIG. 4 is a graphical representation of a fast kVp voltage waveform according to an embodiment of the invention.

FIG. 4 illustrates a plot 300 of dual-kVp switching according to an exemplary embodiment. A pair of voltage levels, kV_L and kV_H, are illustrated along a voltage axis 302 and illustrate levels of a first voltage 305 and a second voltage 310, which is higher than the first voltage 305. An interposer circuit, such as interposer circuit 230 as described above, is configured to rapidly switch or assist in switching between first voltage 305 and second voltage 310. For example, the interposer circuit may rapidly switch or assist in switching between voltages such as 100 kVp and 180 kVp. Plot 300 illustrates an output 313 of the interposer circuit while switching between the first and second voltages 305, 310. While output 313, at second voltage level 310, may "droop" or fall during a view period to a lower voltage level 311, that droop should be no more than 10 kV. An x-ray tube, such as x-ray tube 240 of FIG. 3, connected to receive the output 313 of the interposer circuit, is caused to emit alternating x-ray spectra according to the first and second voltages 305, 310. By acquiring projection data via the alternating x-ray spectra generated at different generator voltage levels, material specific information such as the material composition and effective atomic number of the scanned object can be obtained through a known basis material decomposition process.

A rise time 315 and a fall time 320 are illustrated along a time axis 304. According to an embodiment of the invention, rise time 315 of plot 300 is less than or equal to approximately 10 microseconds. Similarly, fall time 320 is also less than or equal to approximately 10 microseconds. However, in embodiments of the invention, rise and fall times 315, 320 are not so limited and may be greater than or less than 10 microseconds. Additionally, rise and fall times 315, 320 are selected based on operating parameters that result in acquired imaging data having minimal mis-registration between projection pairs. Furthermore, the voltage droop shown in FIG. 4 may be much less than or greater than 10 kV, depending on the type of interposer design.

One skilled in the art will readily recognize that the low and high voltage switching by the interposer circuit may be repeated during scanning at different angular positions of the gantry such that an interleaved pattern of data is acquired with one or more views obtained at the low kVp 305 and one or more views obtained at the high kVp 310.

Figure 5:
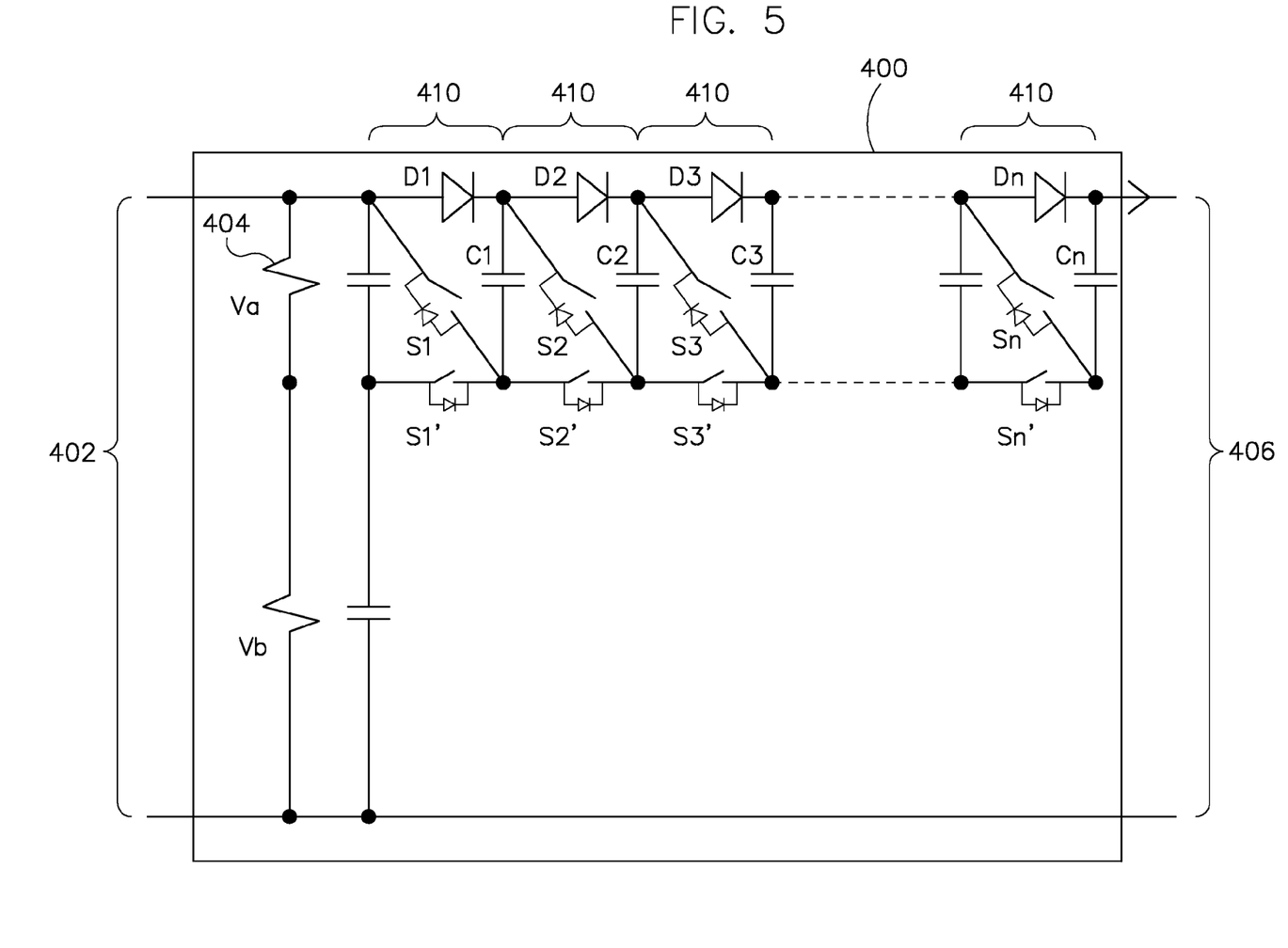
FIG. 5 is schematic diagram of a switching interposer circuit according to an embodiment of the invention.

Referring to FIG. 5, a more detailed view of an interposer circuit is shown according to an embodiment of the invention. Interposer circuit 400 includes a voltage input 402, a voltage divider 404, a plurality of switching stages 410, coupled in series, and a voltage output 406. Each stage has a pair of switches Sn and Sn', a diode Dn operable to block reverse current flow, and a capacitor Cn, where "n" corresponds to the stage number. Under operation, interposer circuit 400 receives a voltage via input 402 from a high-voltage generator such as high-voltage generator 210 of FIG. 3, and the series of stages 410 enables rapid switching of the input voltage between a pair of voltage levels at output 406. That is, switches Sn and Sn' of each stage 410 are controlled by two logic signals, wherein the opening of switch Sn and the closing of switch Sn' acts to output a first voltage, while the closing of the other switch Sn connects the capacitors Cn in series and acts to output a second, higher voltage. The total number of stages 410 depends upon the magnitude of voltage increase, and thus the interposer circuit 400 can be designed to satisfy various voltage level requirements. As with interposer circuit 230 discussed above with respect to FIG. 3, interposer circuit 400 may be a modular circuit and can be removed, repaired, or replaced with little expense or system downtime. Additionally, the individual stages 410 are also modular and can easily be repaired or replaced within interposer circuit 400. In the embodiment shown in FIG. 5, as an example, the interposer circuit controls the voltage applied to the x-ray tube.

Figure 6:
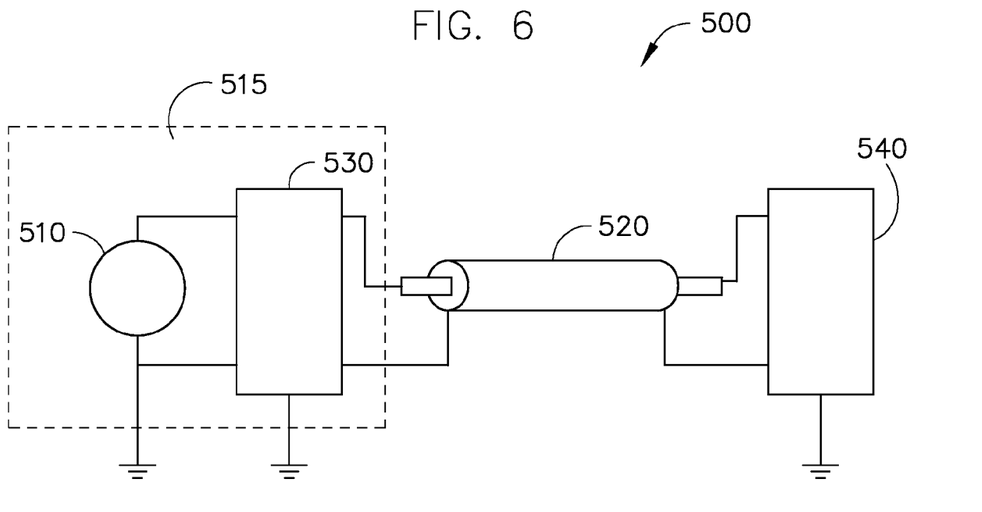
FIG. 6 is a schematic block diagram of a fast kVp switching configuration according to an embodiment of the invention.

FIG. 6 illustrates a fast kVp switching configuration according to another embodiment of the invention. System 500 is configured to operate similarly to system 200 shown in FIG. 3, but with a different placement of the interposer circuit therein. That is, a high-voltage generator 510 is coupled to, or integrated with, an interposer circuit 530, which is then coupled to a high-voltage cable 520. High-voltage cable 520 is thereby directly coupled to an x-ray tube 540. As discussed above with respect to FIG. 3, a modular interposer circuit 530 can be placed in a variety of configurations throughout x-ray system 500 while still operating to rapidly switch voltage levels applied to x-ray tube 540. For example, the high voltage generator 510 and modular interposer circuit 530 can be integrated as a single unit 515, as is shown in phantom in FIG. 6.

Figure 7:
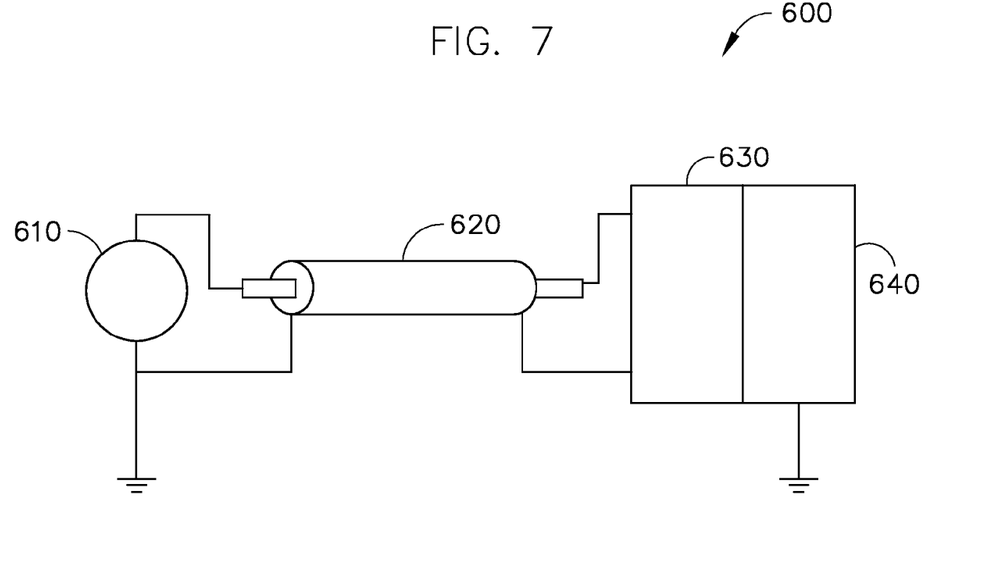
FIG. 7 is a schematic block diagram of a fast kVp switching configuration according to an embodiment of the invention.

As another example, FIG. 7 illustrates a fast kVp switching configuration according to another embodiment of the invention. System 600 includes a high-voltage generator 610 coupled to a high-voltage cable 620. Similar to system 200 shown above in FIG. 3, an interposer circuit 630 is placed after high-voltage cable 620. However, interposer circuit 630 is not only electrically coupled to x-ray tube 640, it is mounted directly to an x-ray tube 640 such that interposer circuit 630 and x-ray tube 640 are operable as a single unit. Interposer circuit 630 could even be integrated into the vacuum region (not shown) of x-ray tube 640 itself.

Figure 8:
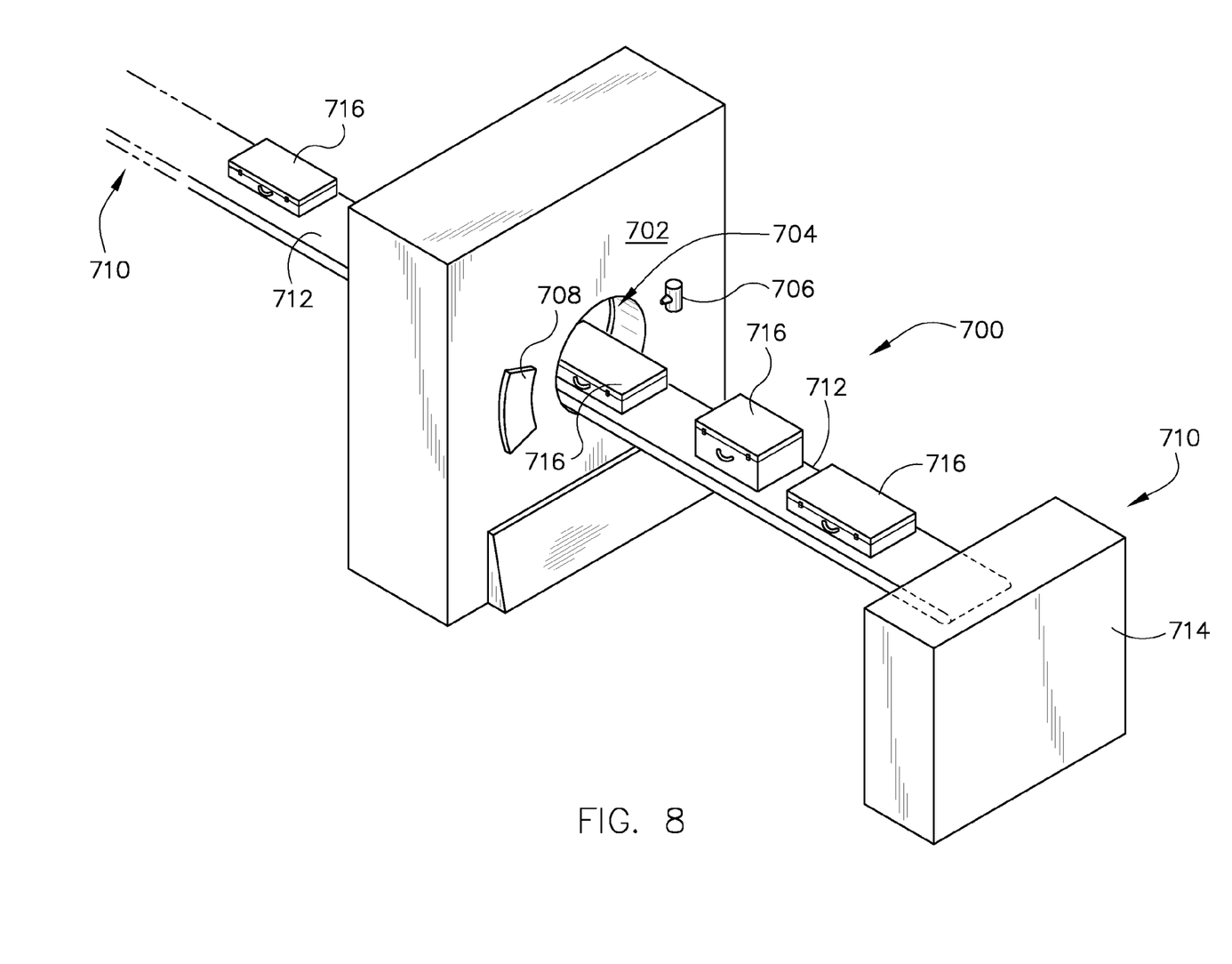
FIG. 8 is a pictorial view of a CT system for use with a non-invasive package inspection system according to an embodiment of the invention.

FIG. 8 is a pictorial view of an x-ray imaging system 700 for use with a non-invasive package or luggage inspection system. The x-ray system 700 includes a gantry 702 having an opening 704 therein through which packages or pieces of baggage may pass. The gantry 702 houses a high frequency electromagnetic energy source, such as an x-ray tube 706, and a detector assembly 708. A conveyor system 710 is also provided and includes a conveyor belt 712 supported by structure 714 to automatically and continuously pass packages or baggage pieces 716 through opening 704 to be scanned. Objects 716 are fed through opening 704 by conveyor belt 712, imaging data is then acquired, and the conveyor belt 712 removes the packages 716 from opening 704 in a controlled and continuous manner. As a result, postal inspectors, baggage handlers, and other security personnel may non-invasively inspect the contents of packages 716 for explosives, knives, guns, contraband, etc. One skilled in the art will recognize that gantry 702 may be stationary or rotatable. In the case of a rotatable gantry 702, system may be configured to operate as a CT system for baggage scanning or other industrial or medical applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed as new and desired to be protected by Letters Patent of the United States is:

1. A system, comprising:
    a generator configured to output at least one voltage level;
    an x-ray source configured to generate x-rays directed toward an object; and
    a modular unit coupled to the output of the generator and to an input of the x-ray source and configured to switch or assist in switching an output to the x-ray source between a first voltage level and a second voltage level, wherein a voltage output of the modular unit is non-sinusoidal, further wherein the system is a CT imaging system.

2. The system of claim 1, comprising a computer configured to:
    acquire imaging data from x-rays generated at the first voltage level and from x-rays generated at the second voltage level; and
    reconstruct at least one image from the imaging data.

3. The system of claim 1, comprising a high-voltage cable coupled between the x-ray source and the generator.

4. The system of claim 3, wherein the modular unit is coupled between the generator and the high-voltage cable.

5. The system of claim 3, wherein the modular unit is coupled between the high-voltage cable and the x-ray source.

6. The system of claim 3, wherein the modular unit is configured to be mounted directly to the x-ray source.

7. The system of claim 3, wherein the modular unit is configured to be integrated into the x-ray source.

8. The system of claim 3, wherein the modular unit is configured to be integrated into the generator.

9. The system of claim 1, wherein a switching time between the first voltage level and the second voltage level is approximately 10 microseconds or less.

10. The system of claim 1, wherein the second voltage level is greater in magnitude than the first voltage level.

11. The system of claim 1, wherein the modular unit is removably integrated between the generator and the x-ray source.

12. A method of acquiring imaging data at more than one energy spectrum, comprising:
    inputting at least one voltage to a modular unit, the modular unit connectable to an x-ray source;
    coupling the modular unit to the x-ray source and outputting a first voltage to the x-ray source;
    projecting a first beam of an x-ray energy spectrum toward an object from the x-ray source, generated using the first voltage, and acquiring a first set of measured projection data;
    switching from the first voltage to a second voltage using the modular unit, wherein a voltage output of the modular unit is non-sinusoidal;
    projecting a second beam of an x-ray energy spectrum toward the object from the x-ray source, generated using the second voltage, and acquiring a second set of measured projection data; and
    reconstructing at least one representative image from the first and second sets of measured projections.

13. The method of claim 12, comprising coupling a high-voltage cable between the modular unit and the x-ray source.

14. The method of claim 12, wherein the switching from the first voltage to a second voltage comprises switching in approximately 10 microseconds or less.

15. The method of claim 12, wherein the second voltage has a magnitude greater than the first voltage.

16. The method of claim 12, comprising determining a material composition of the object from the first set and second set of measured projection data.

17. The method of claim 12, comprising determining one of an effective atomic number and a density of the object from the first set and second set of measured projections.

18. The method of claim 12, wherein the x-ray source is mounted on a rotatable gantry and is rotated about an object to be imaged.

19. An imaging system, comprising:
    a gantry having an opening for receiving a subject to be scanned;
    an x-ray source configured to project x-rays having multiple energies toward the subject;
    a generator coupled to the x-ray source and configured to produce at least one voltage;
    a modular unit coupled between the generator and the x-ray source and configured to provide switching or assistance in switching between a first voltage and a second voltage such that x-rays having a first energy spectrum are generated when applying the first voltage and x-rays having a second energy spectrum are generated when applying the second voltage, wherein a voltage output of the modular unit is non-sinusoidal; and
    a computer configured to acquire imaging data from x-rays at the first energy spectrum and at the second energy spectrum, further wherein the imaging system is a CT imaging system incorporating either a non-rotating or rotating gantry.

20. The imaging system of claim 19, comprising a high-voltage cable coupling the generator to the x-ray source.

21. The imaging system of claim 20, wherein the modular unit is configured to be integrated with one of the generator, the x-ray source, and the high-voltage cable.

22. The imaging system of claim 19, wherein the modular unit is configured to alternate coupling of the x-ray source between the voltages in approximately 10 microseconds or less.

23. The imaging system of claim 19, wherein the x-ray source is one of a single cathode x-ray tube and a dual cathode x-ray tube.

24. The system of claim 1, wherein a difference between the first voltage level and the second voltage level is at least about 50 kVp.

25. The system of claim 1, wherein the generator is configured to output only one voltage level.

26. The system of claim 1, wherein the modular unit comprises:
   a voltage divider; and
   a plurality of switching stages coupled in series.

27. The system of claim 26, wherein each of the plurality of switching stages comprise:
   a plurality of switches;
   a diode operable to block reverse current flow; and
   a capacitor.

28. The system of claim 1, wherein the generator and the x-ray source are in an existing system.

* * * * *

UNITED STATES PATENT AND TRADEMARK OFFICE
CERTIFICATE OF CORRECTION

| | | |
|---|---|---|
| PATENT NO. | : 7,844,030 B2 | Page 1 of 1 |
| APPLICATION NO. | : 12/264428 | |
| DATED | : November 30, 2010 | |
| INVENTOR(S) | : Wilson et al. | |

It is certified that error appears in the above-identified patent and that said Letters Patent is hereby corrected as shown below:

In Column 3, Line 52, below "imaging system." insert -- FIG. 2 is a block schematic diagram of the system illustrated in FIG. 1. --.

In Column 3, Lines 57-58, delete "FIG. 4 is a graphical representation of a fast kVp switching configuration according to an embodiment of the invention."

In Column 7, Line 12, after "system" insert -- 700 --.

Signed and Sealed this
Twenty-first Day of June, 2011

David J. Kappos
*Director of the United States Patent and Trademark Office*